United States Patent [19]

Stackhouse et al.

[11] Patent Number: 4,901,716
[45] Date of Patent: Feb. 20, 1990

[54] CLEAN ROOM HELMET SYSTEM

[76] Inventors: Wyman H. Stackhouse, 3201 Poinsettia Ave., Manhattan Beach, Calif. 90266; Ian M. Williamson, 555 N. Harbor Dr., Redondo Beach, Calif. 90277

[21] Appl. No.: 306,043
[22] Filed: Feb. 6, 1989
[51] Int. Cl.[4] .................................................. A62B 7/10
[52] U.S. Cl. ........................ 128/201.25; 128/201.28; 128/207.12; 128/206.24; 128/DIG. 15
[58] Field of Search .......... 128/206.28, 863, DIG. 15, 128/206.23, 201.28, 201.24, 201.25, 205.24, 207.12, 206.24, 205.17, 201.23, 206.12; 2/173, 436, 15

[56] References Cited

U.S. PATENT DOCUMENTS

| | | | |
|---|---|---|---|
| 1,947,137 | 2/1934 | Fraser | 2/436 |
| 3,020,911 | 2/1962 | Girden | 128/201.15 |
| 3,529,594 | 9/1970 | Charnley | 128/201.23 |
| 3,668,705 | 6/1972 | Garbisch | 2/173 |
| 3,955,570 | 5/1976 | Hutter, III | 128/863 |
| 4,019,508 | 4/1977 | Der Estephaniaa et al. | 128/863 |
| 4,055,173 | 10/1977 | Knab | 128/863 |
| 4,296,746 | 10/1981 | Mason, Jr. et al. | 128/206.24 |
| 4,440,163 | 4/1984 | Spergel | 128/207.12 |

FOREIGN PATENT DOCUMENTS 1461589  12/1966  France .................. 128/DIG. 15

Primary Examiner—Edgar S. Burr
Assistant Examiner—Aaron J. Lewis
Attorney, Agent, or Firm—Singer & Singer

[57] ABSTRACT

There is described a portable and mobile clean room helmet system including a helmet having a removable face shield connected to a battery-powered filtering system for pulling air from within the helmet and exhausting filtered air to the outside environment. The removable face shield contains a plurality of unique flapper valves that allow air to enter the helmet system while at the same time preventing unfiltered air from leaving the system.

9 Claims, 4 Drawing Sheets

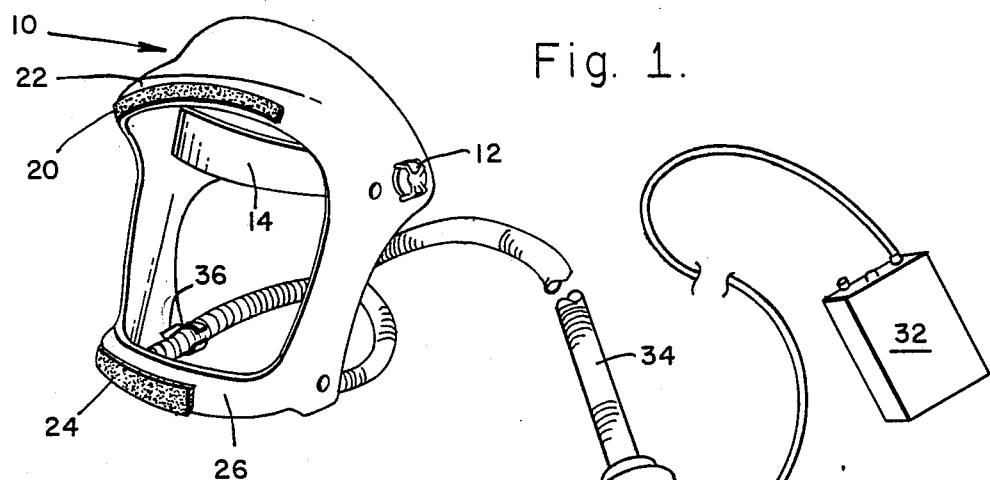
Fig. 1.
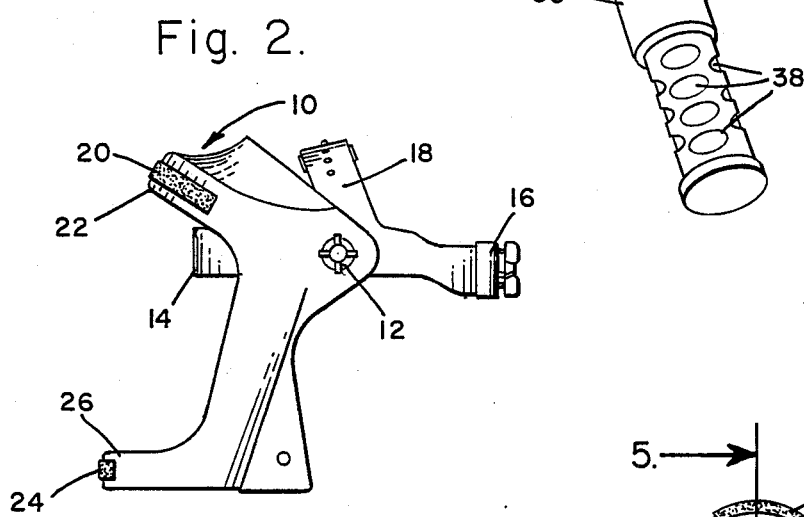
Fig. 2.
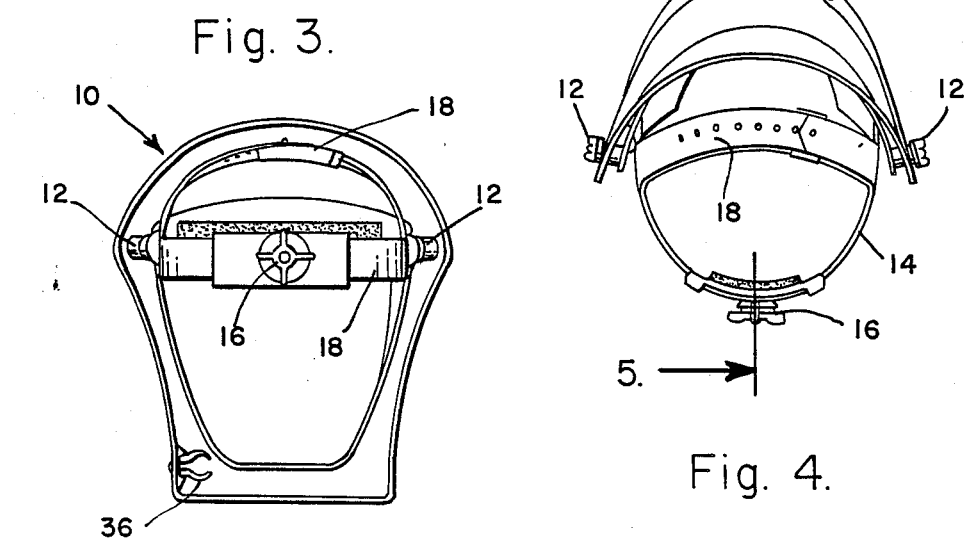
Fig. 3.
Fig. 4.

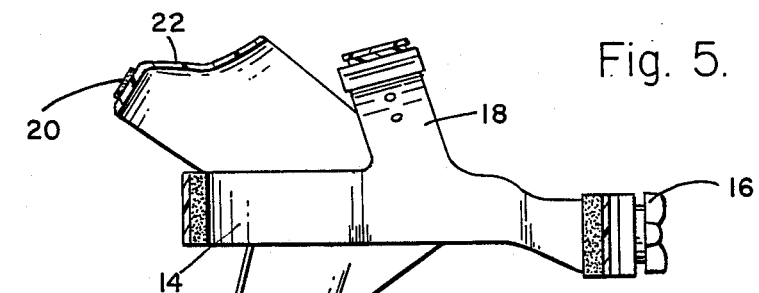
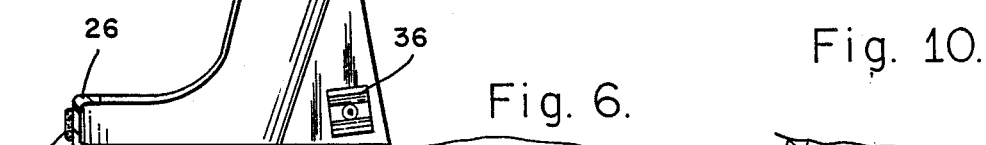
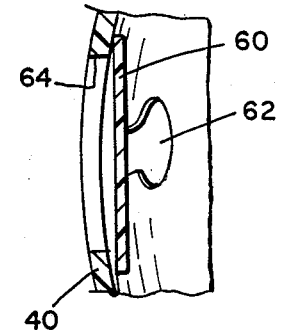
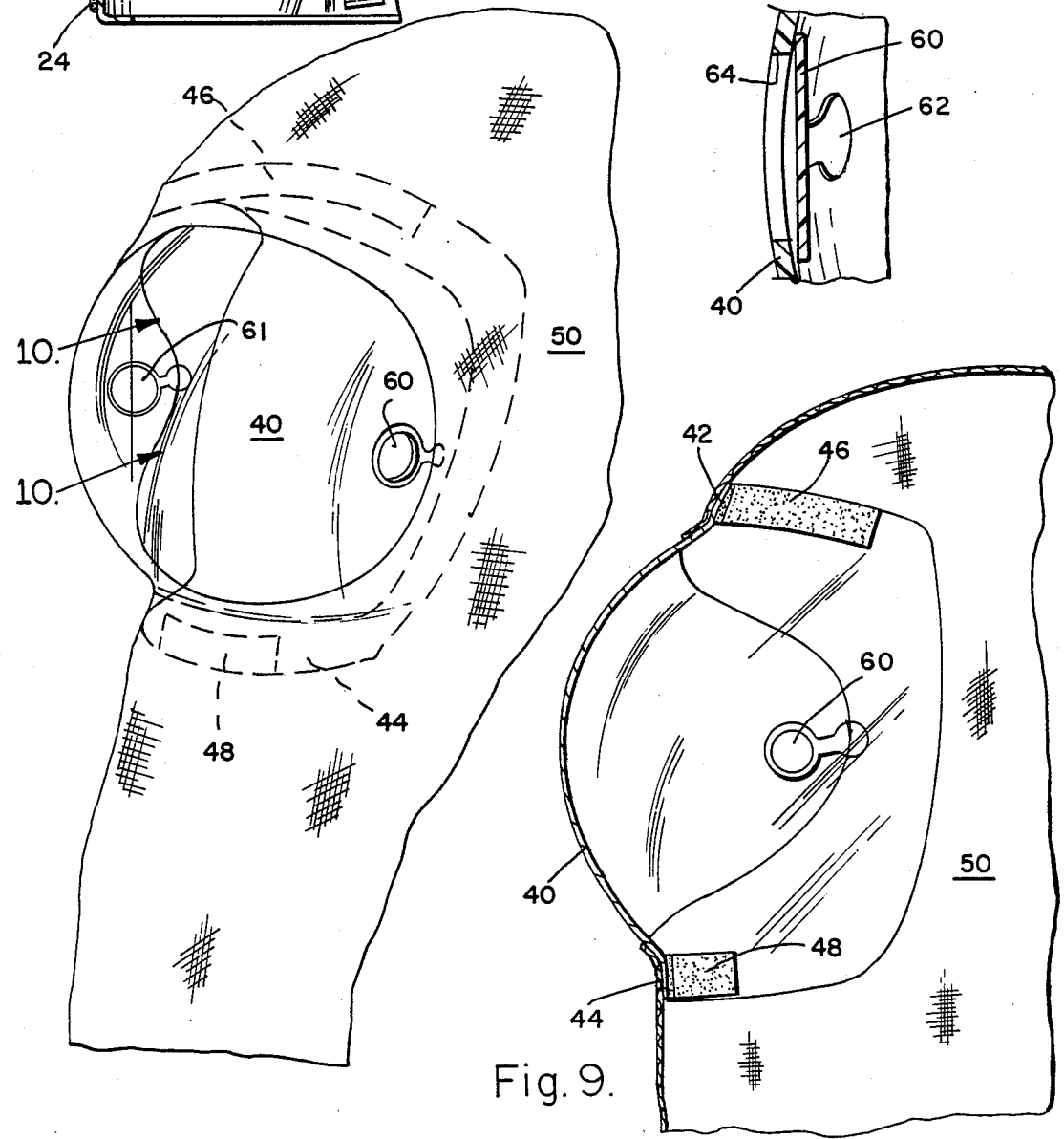

CLEAN ROOM HELMET SYSTEM

This invention is concerned primarily with protecting a clean room environment from the particulate contamination being slouched from a person (SCURF) of human operators that must operate within the clean room environment, and more particularly, to a mobile and portable battery-powered vacuum filtering system carried on a person and which insures that all air and SCURF from the body or surface of the body of the user is properly filtered before entering the clean room environment.

A clean room is generally defined as an area in which particulates and other air suspended items are properly filtered in order to protect the integrity of the clean room environment.

The need for a clean room is obvious when considering a hospital operating room environment where bacteria and particulates can cause infection on a patient and otherwise interfere with the proper recovery of the patient being cared for.

In the industrial environment, a clean room environment is necessary for assembling and manufacturing of such critical items as transistors, IC's and other components that can be seriously affected by particulates and other items suspended in the atmosphere. Impurities and suspended particulates can cause havoc with electronic components or bearings and the like during assembly and manufacture.

Usually the room itself is self-contained having suitable air compressors and filters that recirculate the air and filter the air in an effort to remove suspended items and particulates. With respect to the operators, however, it is necessary that doctors entering an operating room be scrubbed, cleaned and covered in order to prevent particulate and bacteria on the body of the person from being expelled and allowed to enter the clean room itself. The same problem exists with any manufacturing operation having the same requirements for cleanliness whether the clean room is used for manufacturing purposes or for operating room purposes.

This invention is particularly concerned with preventing the body SCURF from leaving the doctor or the person within the clean room environment without being filtered and in particular to filter out all particulates exhaled by the person and at the same time to allow that person free access and movement in order to accomplish his tasks whether it be to operate or to assemble and manufacture.

The prior art has long recognized the need to protect clean room environments from contaminating particulates contained on a person and expelled into the atmosphere from the breath of the person. In the field of medicine, for example, the medical profession has been plagued for many years with the problem of post-operative infection resulting from contamination of open wounds during surgery.

One answer has been the provision of an exhaust type masking system in which the operating personnel are completely covered with a hood and gown of practically impermeable material and which includes a transparent mask located in the opening of the front of the hood. Such a system is described in U.S. Pat. No. 3,955,570.

Another example of a medical application is shown in U.S. Pat. No. 4,019,508 which deals with apparatus for controlling contamination from air expelled by surgeons and other health professionals. In this system there is described aspirators incorporated in a visor and hood arrangement coupled with a flexible conduit connected to vacuum outlets built into the walls of operating rooms. This reference further describes a wearable self-contained and fully mobile personal breathing apparatus adapted to be worn by surgeons or the like and which includes vest means adapted to fit closely about the upper body wearer.

In the area of modern high technology, manufacturing assembly and testing activities, clean rooms have been developed in which air from inside the rooms is carefully cleansed of dust and other particles. As in the medical field, it has been found to be desirable to eliminate as much as possible any contamination emanating from personnel occupying the clean room without overly restricting their movements.

In U.S. Pat. No. 3,525,334 a garment assembly is described having suitable material impermeable to air and wearer generated contamination which includes jacket, pants and a helmet having a visor to enclose and cover the wearer's body. The garment assembly includes air flow means such as a blower, supporter on the wearer having a motor within the suiting and provided with an air intake outside the suiting and an air exhaust within the suiting. Air outflow is provided through a filter disposed within the suiting and occupying the major rear area of the helmet.

These prior art systems tend to be heavy, cumbersome, restrictive and generally make it very difficult for the operator to carry out the tasks within the clean room whether it be to assemble or operate.

In most of these prior art systems, air intake into the helmet is usually occasioned by means of suitable holes within the helmet area or by a separate conduit which may or may not be filtered and which is fed into the helmet area of the user. Experience has shown, however, that these systems have not been entirely satisfactory when considering the proclivities of the user. For example, experience has shown that invariably the user, whether it be a doctor or other operating personnel or an assembler of parts, will through normal habits cough or hiccup which has the result of pressurizing the helmet area and cause exhaust air to fill up the helmet area and be expelled through these same openings that allow air to enter the helmet.

It can be appreciated that allowing unfiltered air from the user's body to enter the clean room environment defeats the whole purpose of a filtering system and gown system as shown by the prior art. The actions of the wearer when coughing, belching, burping, or the like is an involuntary action and is not easily controlled by the wearer, and hence these reflex actions will defeat the complete filtering system and helmet system of the prior art users.

In accordance with the present invention, there is disclosed an improved portable and mobile clean room helmet system in which the problems described and experienced with the prior art have been substantially eliminated. The air intake into and within the helmet system is provided by means of a pair of flapper valves located on each side of the face shield which is removably attached to the helmet. Each flapper valve consists of a substantially thin, flat plastic member covering an annular opening located in the face shield and in which the flapper valve is adapted to pivoted at one end so as to open and close the opening.

In the normal condition, the flapper valve being planer allows air to enter the annular opening in the face shield and provides breathing air for the user. In the event of a reflex action such as a cough, the flapper valve being thin and flexible is immediately urged against the opening and adapts to the contour of the face shield thereby effectively closing and sealing the opening which prevents air from leaving the now pressurized helmet system.

As soon as the reflex action is over, the internal pressure within the helmet is reduced and the flapper valves again opens allowing air to enter the helmey area which air is eventually filtered.

A suitable shroud is attached to the periphery of the face shield and which is long enough to lay on the shoulders of the user for attachment to the gown worn by the user. In this way, the complete helmet system is sealed and air can only enter the helmet system through the defined flapper valves and be exhausted and filtered through the defined exhaust system.

In this way, the invention provides an advantageous means to preclude contamination whether it be hair, skin, cells, makeup, bread particles, etc. released from the worker's head area into the atmosphere without being suitably filtered and at the same time the system allows the wearer complete flexibility and movement to perform the intricate functions of his trade whether he be a physician or an assembler of minute parts.

In accordance with the preferred embodiment of the present invention, there is described a helmet having a support member adjustably sized and shaped to fit the head of the user and which includes an upper horizontal section and a lower horizontal section as an integral part of the helmet.

A hook and pile engaging and holding means such as a Velcro system is located on the external portion of said horizontal section and on the external portion of said lower horizontal section. A curved face shield having an upper peripheral portion conformable generally to the curved upper horizontal section on said helmet and a lower peripheral portion conformable generally to the curved lower horizontal section on said helmet is adapted to protect the face of the user from splashed fluids.

A hook and pile engaging and holding means such as Velcro is also located on the internal upper peripheral portion of said curved face shield and on the internal lower peripheral portion of the face shield for engaging in holding relationship with the hook and pile engaging and holding means located on said upper and lower horizontal section of said helmet respectively. This allows the face shield to be removable from the helmet system.

In the preferred embodiment, at least two flapper valves are located on a curved face shield, one on each side, for allowing air to enter and at the same time preventing air from being exhausted from the helmet without being filtered.

The helmet contains at least one exhaust port communicating with the interior of said helmet that is connected by suitable conduit means to a motor means which includes an electric fan motor and wearable power means for energizing said electric fan motor. The air filtering path includes a filtering means for trapping particulates in the air and exhausting particulate to the outside atmosphere.

Other objects and advantages will be made more apparent by referring now to the accompanying drawings, wherein:

FIG. 1 is a pictorial view of the helmet and filter motor and fan assembly;

FIG. 2 is a side elevational view of the helmet;

FIG. 3 is a rear view of the helmet;

FIG. 4 is a top view of the helmet;

FIG. 5 is a cross-sectional view taken along lines 5—5 of FIG. 4;

FIG. 6 is a pictorial representation of the curved face shield illustrating the flapper valves and the shroud;

FIG. 9 is a section taken along lines 9—9 of FIG. 8;

FIG. 10 is a cross section taken along lines 10—10 of FIG. 6;

FIG. 13 illustrates face shield wrapped within the shroud for protecting the sterilization of the outside of the shroud.

Figure 7:
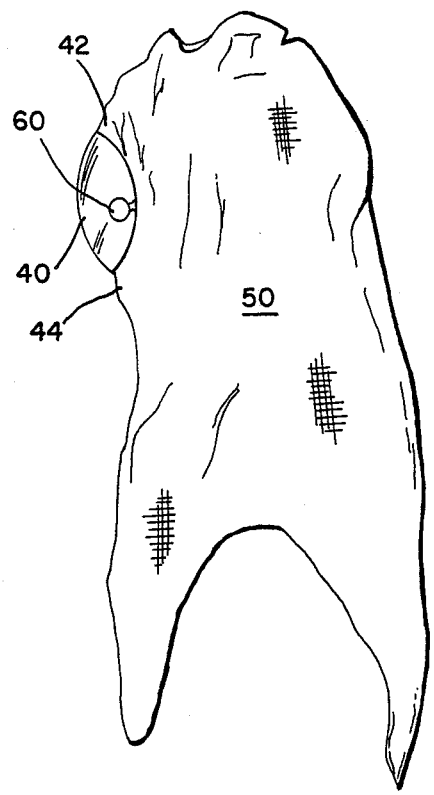
FIG. 7 is a pictorial side view of the shroud and the face mask.
Figure 8:
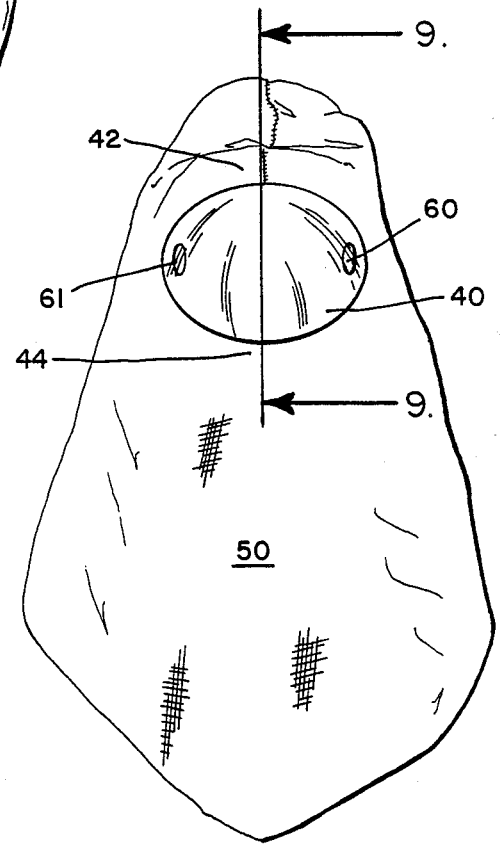
FIG. 8 is a front view of the face shield and the shroud.

Referring now to FIGS. 1, 2, 3, 4 and 5, there is shown a helmet 10 pivotally attached at 12 to a head support member 14 that is adjustable by means of a ratchet arrangement 16 to fit the head of the user. The support member 14 is adapted to fit circumferentially on the head of the user and contains a transverse member 18 that fits over the head thereby adjustably attaching the support member to the head of the user.

The helmet 10 contains a hook and pile engaging and holding means 20 located on the external portion of an upper horizontal member 22 attached to the helmet 10. A hook and pile engaging and holding means 24 is located on an external portion of a lower horizontal section 26 of said helmet 10. Helmet 10 is adapted to be pivotally rotated about pivots 12 in a substantially up and down motion while the support member 14 is attached to the head of the user.

FIG. 1 more fully illustrates how air within the helmet system is exhausted by means of an electric fan motor filter unit 30 attached to a battery pack 32 that is adapted to be worn on the belt of the user. One end of the filter unit 30 contains a conduit 34 that is connected to a holding bracket 36 located within the helmet 10. Air, located within the helmet 10, is sucked out by vacuum through the conduit 34 and is passed through the motor fan filter 30 and is exhausted into the clean room environment through suitable openings 38 located on the filter unit.

Referring now to FIGS. 6, 7, 8 and 9, there is illustrated a curved face shield having a peripheral face portion 40 conformable generally to the curved upper horizontal section 22 on said helmet 10 and a lower peripheral portion 44 conformable generally to the curved lower horizontal section 26 on said helmet 10.

Located on the inside surface of the upper horizontal portion 42 is a hook and pile engaging and holding means 46, for engaging in a holding relationship with the hook and pile engaging and holding means 20 located on the helmet 10. Located on the inside portion of the face helmet 40 opposite the bottommost portion 44 is a hook and pile engaging and holding means 48 adapted to engage in a holding relationship with the hook and pile engaging and holding means 24 located on the lower horizontal section of the helmet 10.

Located on the periphery of the face shield 40 and attached to the outside surface of the face shield along said periphery is a shroud 50 having a length sufficient to hang below the neck and along the shoulders of the user.

The face shield 40 is adapted to be removably attached to the helmet 10 by means of the hook and pile holding and mating surfaces 42 on the face shield mating with the hook and pile surfaces 46 on the helmet and the hook and pile mating surfaces 48 located on the lower portion of the face shield mating with the hook and pile holding and mating surfaces 24 located on the lower portion of the helmet 10. The shroud 50 is adapted to completely cover the user's head including the support member holding the helmet 10 as is more fully shown in FIG. 7.

In the preferred environment, a pair of flapper valves 60 and 61 are located on each side of the face shield 40.

FIG. 10 more fully illustrates the flapper valve 60 and shows it to be a thin, disk of flexible plastic material connected at one point to the inside surface of the helmet at 62 and adapted to cover the periphery of an annular opening 64 located on the face shield 40.

The function of the flapper valve 60 is to allow air to enter through the opening 64 during the normal breathing function of the user. In the presence of a cough, or hiccup or belch or any other involuntary reflex action of the user which might cause a slight pressure to build up within the helmet, the flapper valve 60 will immediately cover and close the annular opening 64 thereby effectively preventing any air from leaving the inside of the helmet area. The flapper valves 60 and 61 will stay closed until the pressure is alleviated at which time the valve will relax and open and allow air to enter as determined by the normal breathing habits of the user.

In this way the flapper valves 60 and 61 prevent unfiltered air from leaving the helmet area without first passing through the portable filtering system 38 as illustrated in connection with FIG. 1.

Figure 11:
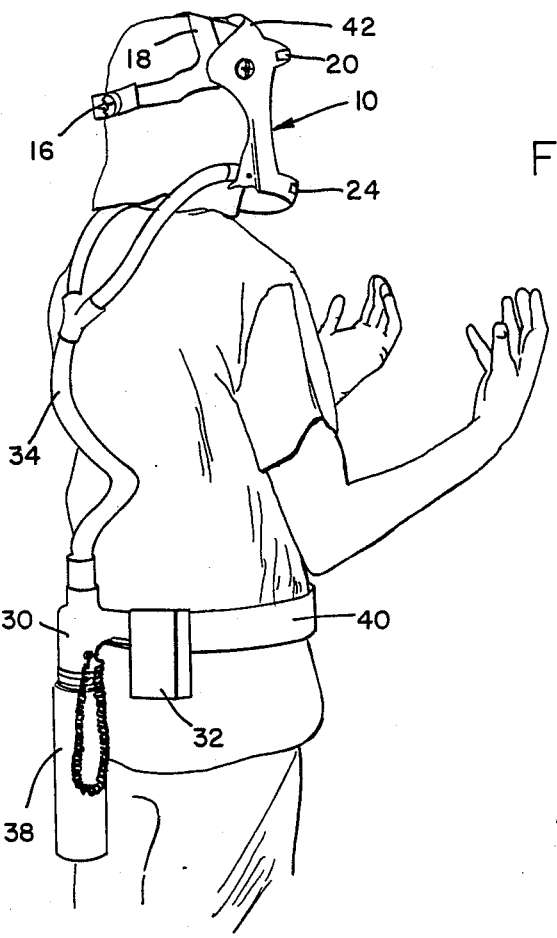
FIG. 11 is a pictorial representation illustrating the helmet, the battery pack and filter system illustrated in FIG. 1 located on the user.

Turning now to FIG. 11, there is shown a pictorial representation of a person, such as a doctor, in a clean room environment, such as an operating room, having the defined invention attached to his body.

Helmet 10 sits on his head considerably adjusted by means of ratchets 16. Helmet 10 is connected by suitable vacuum hose 34 to the fan and motor assembly 30 that is driven by battery pack 32. The air is evacuated by means of motor assembly 30 through filter assembly 38 to the outside atmosphere. The battery pack 32 and the motor assembly 30 is held onto the waist of the doctor by means of a suitable belt 40 thereby making the complete vacuum system mobile and portable and without requiring any additional attention from the user.

Figure 12:
FIG. 12 is a pictorial representation illustrating the face shield and shroud placed over the helmet system as worn by the user.

Referring now to FIG. 12, there is shown how the helmet 60 and shroud 50 are placed over the head of the user so as to completely encompass the helmet 10 as is shown in FIG. 11. Face shield 40 is removably attached to the helmet 10 by means of the mating surfaces of the hook and pile engaging and holding means 20 and 24 in the helmet and the mating hook and pile engaging and holding means on the helmet 10 identified as 46 and 48 as is more fully illustrated in connection with FIGS. 1 through 9.

An assistant is necessary to help the doctor place the shroud and the curved face shield 40 onto the helmet 10 and tie the shroud in place with suitable tie strings. Once the doctor has the helmet 40 and shroud 50 in place and has the unit turned ON, there can be no contamination from any particles eliminated by the doctor into the environment that can harm the patient or the process being worked on.

The shroud 50 and the helmet 40 are packaged in a sterile container with the shroud packaged inside out and around the helmet thereby preserving the sterile condition of the outside portion of the shroud and the helmet when the unit is first opened by the assistant. In this way, when the assistant opens the package, the outside surface is not contaminated or touched while the shroud is unpackaged and placed on the helmet as shown in FIG. 12.

We claim:

1. A clean room helmet system comprising:
    a helmet having a support member adjustably sized and shaped to fit the head of the user and including an upper horizontal section and a lower horizontal section as an integral part of said helmet;
    a hook and pile engaging and holding means located on the external portion of said upper horizontal section and on the external portion of said lower horizontal section;
    a curved face shield having an upper peripheral portion conformable generally to the curved upper horizontal section on said helmet and a lower peripheral portion conformable generally to the curved lower horizontal section on said helmet and adapted to protect the face of the user from splashed fluids;
    a hook and pile engaging and holding means located on the internal upper peripheral portion of said curved face shield and on the internal lower peripheral portion of said face shield for engaging in a mating and holding relationship with said hook and pile engaging and holding means located on said upper and lower horizontal sections of said helmet respectively;
    at least one flapper valve located on said curved face shield for allowing air to enter and at the same time preventing air from being exhausted to the outside atmosphere from said helmet;
    said helmet having at least one exhaust port communicating with the interior of said helmet;
    motor means including an electric fan/motor and wearable power means for energizing said electric fan/motor;
    filter means for trapping particulate in the air and exhausting particulate free air; and
    conduit means coupled with said exhaust port on said helmet, said filter means and said motor means to establish a filtering air path for discharging particulate free air from said helmet to the outside atmosphere.

2. A clean room helmet system according to claim 1 in which said face shield is removeable.

3. A clean room helmet system according to claim 1 wherein said face shield is pivotally mounted to said helmet.

4. A clean room helmet system according to claim 1 wherein said filter element is in the form of a replaceable canister.

5. A clean room helmet system according to claim 1 which includes a pair of flapper valves one located on each side of said face shield.

6. A clean room helmet system according to claim 1 in which said flapper valve comprises a thin flexible plastic disc pivotally attached to the inside of said face shield and adapted to cover an annular opening in said face shield whereby negative pressure within the helmet allows the valve to open and positive pressure within the helmet causes the valve to close.

7. A clean room helmet system according to claim 1 which includes a pair of exhaust ports one on each side of the interior of the helmet connected together with said conduit means.

8. A clean room helmet system according to claim 1 which includes a flexible shroud fixedly attached to the periphery of said face shield and and having a length sufficient to cover the helmet and extend below the shoulders of the user.

9. A clean room helmet system according to claim 8 in which said shroud is initially folded inside out to prevent contamination of the outside area of the shroud prior to attaching the face shield to the helmet.

* * * * *